United States Patent [19]
Plomp

[11] Patent Number: 5,916,609
[45] Date of Patent: Jun. 29, 1999

[54] BAKER'S YEAST AND A METHOD PRODUCING IT

[75] Inventor: Pieter Jan Arnoldus Maria Plomp, Ex Delft, Netherlands

[73] Assignee: Gist-brocades, B.V., Netherlands

[21] Appl. No.: 08/901,312

[22] Filed: Jul. 28, 1997

[30] Foreign Application Priority Data

Jul. 27, 1996 [EP] European Pat. Off. .............. 96202119

[51] Int. Cl.⁶ ....................................................... A23L 1/28
[52] U.S. Cl. ............................ 426/62; 426/549; 426/446; 426/656; 435/255.2
[58] Field of Search .............................. 426/62, 549, 656, 426/446; 435/255.2

[56] References Cited

U.S. PATENT DOCUMENTS

| | | | |
|---|---|---|---|
| 3,032,476 | 5/1962 | Sher | 195/94 |
| 3,914,450 | 10/1975 | Robbins et al. | 426/533 |
| 4,292,330 | 9/1981 | Williams et al. | 426/20 |
| 4,328,250 | 5/1982 | Clement et al. | 426/18 |
| 4,335,144 | 6/1982 | Carduck et al. | 426/62 |

FOREIGN PATENT DOCUMENTS

| | | |
|---|---|---|
| 0 135 208 | 3/1985 | European Pat. Off. . |
| 0 229 976 | 7/1987 | European Pat. Off. . |
| 19 56 146 | 9/1970 | Germany . |
| 32 25 970 | 2/1983 | Germany . |

OTHER PUBLICATIONS

Baker's Yeast, Burrows, S. (1979) *Economic Microbiology*, vol. 4 (Rose, A.H. Ed) pp. 31–64; Academic Press, New York.

Production of Baker's Yeast, Reed, G. (1982) *Prescott & Dunn's Industrial Microbiology*, 4$^{th}$ Ed. (Reed, G. Ed.) pp. 593–633; AVI, Westport, CT.

Production of Baker's Yeast, Chen, S.L. and Chiger, M. (1985), *Comprehensive Biotechnology*, vol. 3 (Blanch, H.W., Drew, S. and Want, D.I.C. eds) pp. 429–461; Pergamon Press, Oxford; Trivedi, N.B.

Baker's Yeast,, Jacobson, G.K. and Tesch, W. (1986), *Crit. Rev. Biotechnol.* 4,75–110.

Developments in Baker's Yeast Production, Beudeker, R.F., Van Dam, H.W., Vander Plaat, J.H. and Vellenga, K. (1990) *Yeast*, (verachtert, H. and De Mot, R. eds.) pp. 103–146; Marcel Deddker Inc., New York.

Zur Zuchtung Von Backhefe in Konzentrierter Melassewurze, Drew, B., Von Specht, H. and Herbst, A.M. (1962), Die Branntweinwirtschaft 102, 245–247.

*Primary Examiner*—Chhaya D. Sayala
*Attorney, Agent, or Firm*—Morrison & Foerster, LLP

[57] ABSTRACT

A process is disclosed for the production of baker's yeast which comprises the fermentation of a baker's yeast strain using a non-molasses carbon source until a fermentation broth having at least 10%, preferably at least 13%, more preferably at least 16% of dry solids content is formed, which can be used directly as a cream yeast without concentration.

21 Claims, No Drawings

BAKER'S YEAST AND A METHOD PRODUCING IT

The invention relates to the production of baker's yeast, in particular a novel yeast composition and a method of producing a concentrated yeast fermentation broth suitable for use as the novel baker's yeast composition.

DESCRIPTION OF THE BACKGROUND ART

The practice of baker's yeast production is well known and amply documented in the literature. Good examples of descriptions of the practice of baker's yeast production are e.g. Burrows, S. (1979) Baker's yeast, Economic microbiology, vol. 4 (Rose, A. H. ed.), pp. 31–64; Academic Press, New York; Reed G. (1982) Production of bakers' yeast, Prescott & Dunn's industrial microbiology, 4th ed. (Reed, G. ed.) pp. 593–633; AVI, Westport, Conn.; Chen, S. L. and Chiger, M. (1985) Production of baker's yeast, Comprehensive biotechnology, vol. 3 (Blanch, H. W., Drew, S. and Wang, D. I. C eds.) pp. 429–461; Pergamon Press, Oxford; Trivedi, N. B., Jacobson, G. K. and Tesch, W. (1986) Baker's yeast. Crit. Rev. Biotechnol. 4, 75–110; and Beudeker, R. F., Dam, H. W. van, Plaat, J. H. van der, and Vellenga, K. (1990) Developments in Baker's yeast production, Yeast (Verachtert, H and De Mot, R. eds.) pp. 103–146; Marcel Dekker Inc., New York. Below, further attention will be given to specific aspects of the production and use of baker's yeast that can be improved with the invention described in this specification.

After the production of the seed yeast in multiple stages (Chen, S. L. and Chiger, M. (1985) Production of baker's yeast, Comprehensive biotechnology, vol. 3 (Blanch, H. W., Drew, S. and Wang, D. I. C eds.) pp. 429–461; Pergamon Press, Oxford) the production of the so-called commercial yeast follows. In standard practice this is done in fed-batch fermentations mainly using molasses as the C-substrate and ammonia or urea as the main nitrogen source. The substrates are fed to the fermenter during the fermentation. Other growth requirements like phosphate, part of the nitrogen, salts and vitamins are added to the fermenter at the start of the fermentation or in the very first hours of fermentation. Molasses functions also as the source of many trace elements, that are dosed in sufficient or even excessive amounts by feeding the molasses as C-source. The fermentation takes between 10 and 20 hours and ends with a broth containing between 4 and 8% dry yeast solids.

Before it can be used, the molasses needs to be clarified. This means that the molasses is diluted in order to lower the viscosity and make the molasses pumpable, but also to allow removal of sediment (sand, dirt, colloidal matter) before sterilization and feeding to the fermenter.

The feed schedules used for the molasses and nitrogen source and to some extent also the other growth requirements are generally considered as critical knowledge and not much is published about the schedules actually used in industrial practice. It is clear however that the schedules are of prime importance for the final yeast quality obtained. As is clear from Burrows, S. (1979) Baker's yeast, Economic microbiology, vol. 4 (Rose, A. H. ed.), pp. 31–64; Academic Press, New York, and earlier work of Drew, B. von, Specht, H. and Herbst, A. -M. (1962) Zur Züchtung von Backhefe in konzentrierter Melassewürze. Die Branntweinwirtschaft 102, 245–247, higher molasses feed profiles lead to more active yeast and lower molasses feed profiles to less active yeast having a longer shelf-life. In current practice, the maximal feed rate is limited on the one hand by the oxygen transfer rate (OTR) of the fermenter and on the other hand by the critical growth rate of the yeast above which formation of alcohol starts. Formation of alcohol is undesirable because of the resulting poor keeping quality of the yeast and loss of yield on carbon source. Apparently a too low molasses feed profile relative to the amount of yeast in the fermenter can lead to too low gassing activity of the yeast. Thus in Sher, H. N. (1962) Continuous process for the production of yeast, U.S. Pat. No. 3,032,476, it is stated that the growth rate of the yeast should be maintained above 0.05 $h^{-1}$ and preferably even above 0.075 $h^{-1}$. So, given an economically relevant inoculum percentage, the minimum growth rate considered necessary for good gassing performance together with the maximum feed rate due to fermenter oxygen transfer rate limitations forms the basis for the maximum fermentation time of 20 h as stated by Chen, S. L. and Chiger, M. (1985) Production of baker's yeast, Comprehensive biotechnology, vol. 3 (Blanch, H. W., Drew, S. and Wang, D. I. C eds.) pp. 429–461; Pergamon Press, Oxford.

After the fermentation the yeast cells are washed thoroughly by repeated concentration and dilution. Typically a centrifugally concentration is done to a suspension of about 20% dry solids and the suspension is at least once diluted to more than 100% of the original volume, resulting in a non-yeast solid concentration in the free liquid of less than 10% of the concentration in the free liquid phase of the fermentation broth. Thus, a cream yeast is obtained with a yeast dry solids concentration of 18–22% which is either sold directly as cream yeast or further processed into block-yeast or granulated yeast (25–36% dry solids) or dried to obtain active dry yeast or instant dry yeast with up to 97% yeast dry solids. The extracellular water removed from the broth in this way amounts to about 50% for cream yeast, up to almost 100% for the dried yeast. Together with the water required to wash away non-fermented solids from the molasses, this water forms a large stream of waste-water that needs to be handled. Nowadays full waste-water treatment includes an evaporation plant concentrating the waste-water stream and yielding vinasse. At the expense of a high energy input, this step removes about 80–95% of the biological oxygen demand (BOD) from the waste-water stream. The remaining BOD is treated in an anaerobic waste-water treatment plant and subsequently in an aerobic waste-water treatment plant, again at considerable cost. Moreover, these costs will increase in the future as energy becomes more expensive and also demands for treatment of waste streams increase for environmental reasons.

SUMMARY OF THE INVENTION

The invention relates to the production of baker's yeast, in particular a novel yeast composition and a method of producing a concentrated yeast fermentation broth suitable for use as the novel baker's yeast composition.

According to the invention a method of production and a novel baker's yeast composition is disclosed for producing a concentrated yeast fermentation broth suitable for use as the novel baker's yeast composition having a dry yeast solids content of 10 to 22%, preferably 13 to 22%, more preferably 16%–22% and an aqueous phase with the fermentation components consisting of medium components and metabolites of the yeast. This is preferably achieved by (a) starting a fed batch fermentation by feeding seed yeast with a suitable carbon and nitrogen source and other nutrients essential for yeast growth, and (b) continuing fermentation until the dry yeast solids content of the fermentation broth is 10–22%, and (c) optionally concentration of the broth to 16–22%, for example, by centrifugation and use of the aqueous phase in the preparation of a following fermentation.

DETAILED DESCRIPTION OF THE INVENTION

The new process for the fermentation and production of baker's yeast on an industrial scale starts with a suitable seed yeast, the quality and amount of which should be more or less equal to conventionally used seed yeast. Thus no special requirements exist in this respect. The present process is preferably carried out on an industrial scale. In practice, fermentors of 50–300 m3 will be used for fed-batch fermentation either bubble-column or stirred, under normal or increased pressure, to obtain adequate oxygen transfer rates to supply the growing yeast with oxygen. The process of the invention produces a concentrated fermentation broth in existing, industrial baker's yeast fermenters, without demanding very high oxygen transfer capacities. By baker's yeast is meant a commercially or industrially produced *S. cerevisiae* strain.

Growth in the fermenter is sustained by feeding an adequate non-molasses carbon source (e.g. glucose, fructose, sucrose, maltose, dextrines maltotriose, raffinose or alcohol or any mixture thereof) with a sufficiently high concentration of carbon present in the feed. The concentration in the feed should be sufficiently high to obtain the required dry yeast solids concentration, taking into account the required starting volume of the fermenter. Typically the sugar concentration in the feed will be 250 g/l or higher, but for ease of handling preferably between 400 and 600 g/l of sugar.

The nitrogen source can be any conventional nitrogen source used for the normal practice of baker's yeast production, or any C/N-source rich in hydrolyzed proteins (e.g. casamino acids, trypton, pepton, soy meal) or a combination thereof. The N-dose should be sufficiently high to be non-limiting. The total feed of consumable N can be determined on an elemental balance to obtain protein contents (Kjeldahl N * 6.25) of 40–60%. The precise concentration is less critical than for the carbon source. A 25% solution of ammonia or any other nitrogen source equivalent in N-concentration will normally suffice, but other concentrations, preferably higher, can be used.

Phosphate and other nutrients like salts and vitamins and other processing aids of food-grade quality can be used according to the current practice, as described in the open literature, taking care of not to overdose the components.

All nutrients described above are typically added in the form of relatively pure components like sugar syrups, ammonia, phosphoric acid, etc, but can also be added in a less pure form as long as the addition does not contain any component that needs to be washed out in order to make the yeast obtained suitable for the application in food or feed. The components can be combined in a way that favours the metabolite composition of the aqueous phase of the fermentation broth with respect to the taste and flavour of the product.

Feeding to the fermenter starts after addition of the seed yeast. At least the carbon and nitrogen sources are fed to the fermentation, except for a small portion that may be given batch-wise at the start of the fermentation. The other nutrients like the phosphate source, salts and vitamins can also be fed to the fermenter, either in part or completely. Feeding of these components, either separately or mixed with the carbon and/or nitrogen source has the advantage that very high concentrations at the start of the fermentation are avoided. It is however possible to add these nutrients at the start of the fermentation especially when the carbon and nitrogen sources are of a high concentration thus allowing for a relatively large starting volume of the fermenter.

The feed schedule for the carbon source is such that the starting feed-rate is adapted to the rate at which the seed yeast can start growing (most conveniently expressed in growth rate) and then increases until the maximal feed rate for the carbon source is reached. This maximal feed rate for the carbon source is on the one hand determined by the maximum oxygen transfer rate of the fermenter and on the other hand by the critical growth rate of the yeast, above which production of alcohol starts. Clearly when the latter is limiting the feed rate can still be increased exponentially due to growth of the yeast until the oxygen transfer rate of the fermenter becomes limiting. Control of the feed rate should be tight enough to prevent alcohol concentrations higher than 1% and preferably the alcohol concentration should remain below 0.5%. Near the end of the fermentation the feed rate may be reduced below the maximal value in order to allow consumption of poorly fermentable C- and C/N-substrate or alcohol. The feed-rate may be stopped altogether for some period at the end of the fermentation in order to reduce the number of buds (ripening of the yeast).

The nitrogen feed may be scheduled in any convenient way, e.g. to minimize the use of chemicals for pH control, as long as the nitrogen does not become limiting for the growth of biomass. Like over-feeding of the carbon substrate, under-feeding of the nitrogen source will lead to excessive alcohol formation. This can be most easily avoided by feeding the nitrogen source proportional to the carbon source or higher, especially in the early phases of the fermentation. Alternatively, part of the nitrogen may be added prior to seeding. The nitrogen feed is stopped when the total required amount of nitrogen is fed to the fermenter, which can be easily calculated from the N-balance over the fermentation. The same holds for feed schedules of other nutrients like phosphate, salts and vitamins if these are not added before seeding.

The temperature is maintained between 20 and 45° C., preferably between 25 and 36° C. The pH is maintained between pH 3 and 8, preferably between pH 4 and 7, e.g. pH 5.5.

The fermentation is continued until the required concentration of dry matter is reached which is 10%, more preferably 13%, dry yeast solids or higher, preferably 16% dry yeast solids or higher. With the feed rates used, this takes a fermentation time of typically over 20 hours and more typically a fermentation time of 30–50 hours will be required. Specific growth rates at the end of the fermentation will typically drop below 0.05 h$^{-1}$ for an extended period of at least 5 hours.

After the fermentation, the concentrated broth is transferred to a storage vessel and cooled to low temperature, preferably 0–10° C. and more preferably 0–4° C. If the dry matter concentration is between 10 to 16% of yeast biomass a centrifugational concentration step may be applied resulting in a more concentrated fermentation broth and an aqeous phase. The aqueous phase is then used in the next fermentation as the filling water, saving the nutrient components. Preferably, no washing is done.

The concentrated fermentation broth obtained is the new baker's yeast product according to the invention and is a special cream yeast that can be used by the baker in the same manner as conventional cream yeast.

The special cream is either sold directly as normal or stabilized special cream yeast (EP-A-461725) or used to produce block yeast or dried yeast, either active dry yeast or instant dry yeast, using any suitable process.

The special cream yeast made by the process of the invention can however be easily distinguished from a conventional cream yeast because the composition of the extracellular phase is quite different. In the conventional creams with 18–22% yeast dry solids typically the total concentration of the dissolved solids will be less than 0.1 osmol/kg (as measured by freezing point depression by example by the Osmomat 030 of Gonotec) and preferably less than 0.025 osmol/kg (see for osmol eg. Webster's new collegiate dictionary). The concentrations depend strongly on the efficiency of washing of the cream yeast, unwashed creams containing high concentrations and extensively washed cream yeast containing very low concentrations. Typically the composition of the conventional cream exists of non-fermentable components from the (beet)molasses and metabolites produced by the cells or leaking from the cells during storage. Mainly succinic acid and acetic acid are found together with small amounts of betaine, pyrrolidin carboxylic acid and potassium- and sodium-salts and other salts in the typical ratio's of the molasses feed and consumption thereof by the yeast. A special cream yeast obtained by a process of the invention contains besides yeast solids in the extracellular fraction a multitude of organic substances derived from yeast metabolism and organic substances and mineral components originating from the medium. The total concentration of dissolved solids will be higher than 0.2 osmol/kg and more preferably higher than 0.4 osmol/kg. An excessive amount of salts, as seen in the use of molasses is typically avoided. In addition to nonconsumed salts and other medium compounds many yeast metabolites are found which beneficially affect the taste and flavour properties of bread products made with such yeast. Those components are products of the yeast metabolism comparable to the production of components during the fermentation of dough, like glycerol, succinic acid, isobutyric accid, α-ketoglutaric acid aminoacids, acetic acid, vitamines etc. These components may include polysaccharides, that can be detected easily with e.g. NMR techniques. The concentrations of these components are typically in the range of 0.1 to 1 gram/liter aqueous phase or higher for components like succinic acid and pyruvate.

The clear advantage of the process of the invention is that it completely abolishes the production of waste water in the production of cream yeast and more than halves the production of waste water for other formulations of yeast like blocks, granulated or dried yeast.

Another advantage is that there is no need to wash the yeast from the fermenter in the separators in contrast to current practice where yeast produced with molasses is extensively washed to remove unwanted components from the molasses originating from the processes used in the sugar mill. This not only gives another saving in wastewater, but also greatly reduces the amount of high quality water needed for the production of yeast.

This amounts to a very significant cost-saving as the total cost associated with the treatment of waste-water and use of drinking-quality water may run up to 25% of the cost-price of baker's yeast produced in conventional manner depending on local regulations. Important is that this cost-saving will only tend to increase in the future as it is based on saving in energy use and use of clean (drinking) water, both of which are expected to become more scarce and expensive in the future. As also demands on waste-water treatment will increase in the future due to higher demands on the purity of the water released into the environment, also the costs associated with the biological treatment of waste-water will increase in the future. Again, the process of the invention helps to avoid such increase costs having a substantial impact on baker's yeast production.

Furthermore, problems that may be anticipated from the literature have been overcome by the described process. Thus, it was surprisingly found that, the product obtained in the process of the invention does not have the disadvantage of low gassing activity due to the long fermentation time at low growth rates. The novel yeast composition obtained at the end of fermentation in accordance with the invention is active enough to be used in the normal way by the baker. The activity is typically higher than 10 ml gas produced in 3 hours by an amount of yeast containing 1 mg Kjeldahl nitrogen in a normal lean dough (see Examples). Preferably the gassing activity of such a yeast preparation is comparable to that of a conventional cream yeast preparation.

Yet another problem that can be encountered is related to the maintenance energy required to maintain yeast integrity (Herbert, D. (1959); Recent progress in Microbiology (Tunevall, G. ed) pp. 381; Pirt, S. J. (1965) Proc. R. Soc. Lond. Ser. B 163, 224). Like the energy for growth it is derived from the carbon substrate but it is not used for conversion of carbon substrate into yeast dry matter but instead is used to maintain the integrity of the yeast cell (Tempest, D. W. and Neyssel, O. M (1984) The status of $Y_{ATP}$ and maintenance energy as biologically interpretable phenomena. Ann. Rev. Microbiol. 38, 459–486). Among other things this includes the energy required to maintain the concentration gradients for various salts between the cell interior and exterior. Increase of the concentration of biomass in a conventional process with molasses as substrate would lead to significant loss of yield. Such a loss of yield is not found, due to the avoidance of excessive salt concentrations.

Also a clear advantage is that the special cream yeast obtained by this process still contains a high concentration of yeast metabolites which in a conventional cream yeast are washed away or not produced at all. These metabolites retained in the product will enhance the nutritional value and also the taste and flavour of the products made with the yeast.

It is implicated that the invention extends not only to the special cream yeast obtainable by a process of the invention, but also to other yeast preparations derived from such a special cream yeast (e.g. blocks, granulated yeast, active instant dry yeast), flour doughs incorporating such yeast preparations and baked products derived therefrom.

EXAMPLES

Nutrients used in the fermentation process
Carbon source

As carbon source a 60% glucose solution can be used. Alternatively a commercial sugar syrup can be used containing 58% dry matter, of which 47% glucose, 0.1% fructose, 5% disaccharides, 2% trisaccharides and 4% other components.
Nitrogen source As nitrogen source a 50% urea solution can be used or also a 25% ammonia solution or a combination of a 25% ammonia solution and a dosage of trypton or a mixture of selected amino acids.
Phosphate source As phosphate source it is most convenient to use phosphoric acid but also mono- or diammoniumphosphate can be used.

Salts, trace elements and vitamins

In case of the use of carbon substrates (in part or for the total feed to the fermentation) that do not contain salts, trace elements or vitamins, these need to be supplemented. In the literature ample information is available about the composition of the growth media. The composition in general depends on the strain and the type of process where one should aim for the lowest possible supplementation in order to save costs.

A useful addition per kg of glucose equivalents is: 24 g $K_2SO_4$; 12 g $MgSO_4·7aq$; 1.6 g $CaCl_2·2aq$; 25 mg vitamin B1; 1.25 mg vitamin B2; 95 mg vitamin B5; 12 mg vitamin B6; 0.5 mg biotin; 5.8 mg p-aminobenzoic acid; 40 mg nicotinic acid; 40 mg nicotinamide; 1.44 g inositol; 1025 mg $Fe(NH_4)_2(SO_4)_2·6aq$; 192 mg $ZnSO_4·7aq$; 30 mg $CuSO_4·7aq$; 17 mg $MnSO_4·aq$; 23 mg $H_3BO_3$; 23 mg $Na_2MoO_4·2aq$; 11 mg Kl; 43 mg Ribitol.

Fermentation recipe
Additions

Using the above media a fermentation can be designed with the following total additions for a final volume of 6 liter: 55 g dry yeast solids seed yeast; 2950 g glucose equivalents; 125 g N, 44.5 g $P_2O_5$ equivalents with supplementation of salts, trace elements and vitamins as explained above.

Feed schedules

The carbon source is fed in such a way that the specific growth rate increases from 0.08 $h^{-1}$ to 0.21 $h^{-1}$ in 6 hours of fermentation. From then on the carbon source feed rate is increased exponentially until the maximal feed rate to the fermenter is reached (depending on the maximal OTR of the fermenter). From then on the carbon feed rate is kept constant until the total required amount of carbon is fed to the fermenter. In a standard fermenter this typically takes 40–50 hours of fermentation.

The nitrogen is fed in ratio to the carbon feed or at constant rate until the end of the fermentation. If necessary the feed can be stopped earlier thereby creating the possibility to increase nitrogen concentrations in the broth early in the fermentation to enhance nitrogen assimilation for strains that require this.

Other fermentation parameters

The pH is kept constant at pH 5.5, the temperature is kept constant at 32° C. Aeration is done in such a way that the dissolved oxygen concentration is 2% of the saturation value or higher.

Fermentations with a concentration step

The process can be performed as described above. The feed is continued to 20 hours, resulting in 12% yeast dry matter. The fermentation broth is concentrated in a separator resulting in a special cream yeast of 20% yeast dry matter and about 0.4 kg of aqeous phase. The aqueous phase is used in the next fermentation as starting phase of the fermentation. The addition of the medium components, especially of the salts, can be decreased with the amounts already available in the aqueous phase of the separator. In a series of successive fermentations the composition of the special cream yeast product will be in equilibrium an be about the same as for the product without the separations step.

Product characterization
Composition extracellular water phase

The chemical composition of the yeast is very similar to normal baker's yeast. A dry matter content of 16% was obtained. The composition of the extracellular water phase is however clearly different which can be seen e.g. in an NMR spectrum of the supernatant of a special cream yeast produced as described in this example, using pure glucose as carbon substrate in a 45 h fermentation process. In contrast to a conventional cream yeast, we found that the amount of succinic acid and polysaccharides was increased in the product according to the present invention besides a multitude of components as described before. An osmotic value of 0.8 osmol/kg was obtained in contrast with osmotic values of 0.025 osmol/kg or less for standard cream yeast.

Gassing test in dough

To test the gassing activity, a normal lean dough is prepared. Relative to the amount of flour, the dough contains 55% water, 2% salt and 0.45% dry yeast solids. The dough is mixed in a normal way to get a properly developed dough and then put in a gas-production measurement device essentially as described by Burrows and Harrison (1959) at 28° C. and incubated for up to 3 hours. The amount of gas produced is recalculated to the amount of gas produced by a quantity of yeast containing 1 mg of nitrogen determined according to Kjeldahl over 3 hours time. After recalculation, the amount of gas was 14 ml. The amount of gas produced by a regular cream yeast under these conditions is 15 ml.

I claim:

1. A baker's yeast composition having a cellular and extracellular water phase component prepared under carbon limiting conditions wherein the non-molasses carbon feed rate is controlled to prevent alcohol concentrations higher than 1% during fermentation comprising:

baker's yeast having a dry yeast solids content between 10–22%; and an extracellular phase containing yeast metabolites and organic compounds and salts with a concentration range of about 0.2 to 0.8 osmol/kg.

2. A composition according to claim 1 suitable for use as a cream yeast and having a dry solids content of 16–22%, or suitable for use as a compressed yeast and having a dry solids content of 26–38%, or suitable for use as a dry yeast or active dry yeast and having a dry solids content of 90–98%.

3. A flour dough which comprises a yeast composition according to claim 2.

4. An improved method to make bread wherein the improvement comprises employing the composition of claim 2.

5. A flour dough which comprises a yeast composition according to claim 1.

6. A baked product prepared using a flour dough according to claim 5.

7. An improved method to make bread wherein the improvement comprises employing the composition of claim 1.

8. A method of producing a yeast fermentation broth suitable for direct use as a baker's yeast which comprises (a) starting fermentation by feeding seed yeast with a suitable non-molasses carbon and nitrogen source and other nutrients essential for yeast growth, and (b) continuing fermentation until the dry yeast solids content of the fermentation broth is 10–22%.

9. A method according to claim 8 which comprises:

feeding seed yeast with a carbon source at an initial rate to enable commencement of yeast growth and then increasing the feed rate of the carbon source so as to achieve the maximal carbon source feed rate while maintaining the alcohol concentration at not higher than 1% at a temperature of 20–45° C. and a pH of 3–8.

10. A method according to claim 9 wherein the fermentation time is more than 20 hours.

11. A method according to claim 9 which comprises continuing fermentation until the dry yeast solids content of the fermentation broth is about 10–22%, either maintaining the maximal carbon source feed rate or maintaining the maximal carbon source feed rate for a period followed by reducing the carbon source feed rate to achieve consumption of poorly fermentable carbon substrate and/or alcohol.

12. A method according to claim 9 which further comprises addition of a stabilizing agent to obtain a yeast preparation suitable for direct use as a stabilized cream yeast.

13. A method according to claim 9 which comprises further processing to obtain block yeast or granulated yeast or drying to obtain active dry yeast or instant dry yeast.

14. A method according to claim 8 which comprises continuing fermentation until the dry yeast solids content of the fermentation broth is about 10–22%, either maintaining the maximal carbon source feed rate or maintaining the maximal carbon source feed rate for a period followed by reducing the carbon source feed rate to achieve consumption of poorly fermentable carbon substrate and/or alcohol.

15. A method according to claim 8 wherein the specific growth rate of yeast at the end of the fermentation is below $0.05 \text{ h}^{-1}$ for an extended period of at least 5 hours.

16. A method according to claim 8, which further comprises concentration of fermentation broth to 16–22% dry solids content.

17. A method according to claim 16 whereby the aqueous phase originating from the concentration is used in a following fermentation.

18. A method according to claim 8 which further comprises addition of a stabilizing agent to obtain a yeast preparation suitable for direct use as a stabilized cream yeast.

19. A method according to claim 8 which comprises further processing to obtain block yeast or granulated yeast or drying to obtain active dry yeast or instant dry yeast.

20. A method according to claim 8 wherein in step (b), the dry yeast solids content of the fermentation broth is 13–22%.

21. A method according to claim 8 wherein in step (b), the dry yeast solids content of the fermentation broth is 16–22%.

* * * * *